United States Patent [19]

Cilladi et al.

[11] Patent Number: 4,829,992
[45] Date of Patent: May 16, 1989

[54] SOFT PLAYING ORTHOPEDIC SPLINT

[76] Inventors: David R. Cilladi, R.D. #1, Brockport, Pa. 15823; Jeffrey C. Sunderlin, #30 Windcave R.R. #1, Springfield, Ill. 62707; Steven R. Tippett, 1305 W. Pine, Chillicothe, Ill. 61523; Patrick B. Karns, 6500 University Apt. 209, Peoria, Ill. 61614

[21] Appl. No.: 103,540

[22] Filed: Oct. 1, 1987

[51] Int. Cl.$^4$ ............................. A61F 5/04
[52] U.S. Cl. ....................... 128/90; 128/80 R; 128/157; 2/22; 264/216; 428/451
[58] Field of Search ............ 2/2, 2.5, 22; 128/80, 128/80 C, 89 R, 90, 157; 264/216, 222; 428/451, 452

[56] References Cited

U.S. PATENT DOCUMENTS

| | | | |
|---|---|---|---|
| 3,301,252 | 1/1967 | Mahoney, Jr. | 128/90 |
| 3,621,489 | 11/1971 | Keller | 2/22 |
| 3,797,047 | 3/1974 | Pillet . | |
| 3,819,796 | 6/1974 | Webster et al. | 128/90 |
| 4,169,469 | 10/1979 | Arluck | 128/90 |

OTHER PUBLICATIONS

Bergfeld et al, The American Journal of Sports Medicine, vol. 10, No. 5, (1982), pp. 293–296.
Bassett, III et al, The American Journal of Sports Medicine, vol. 7, No. 6, (1979), pp. 358–360.

Primary Examiner—Richard J. Apley
Assistant Examiner—Paul Prebilic
Attorney, Agent, or Firm—Kinzer, Plyer, Dorn, McEachran & Jambor

[57] ABSTRACT

Soft orthopedic splint comprising an inner layer of RTV silicone rubber impregnated gauze and an outer layer of silicone rubber impregnated gauze with a soft foam pad interposed between. The soft pad has spaced edges which define a seam area to be filled by the rubbery compound. The pad is also provided with openings into which the rubber exudes before vulcanizing so that the intermediate pad is locked or keyed in place without using cement. The splint is split along the seam so that the split edges are entirely rubber surfaces covering the pad. The ends of the pad are also covered by rubber.

4 Claims, 2 Drawing Sheets

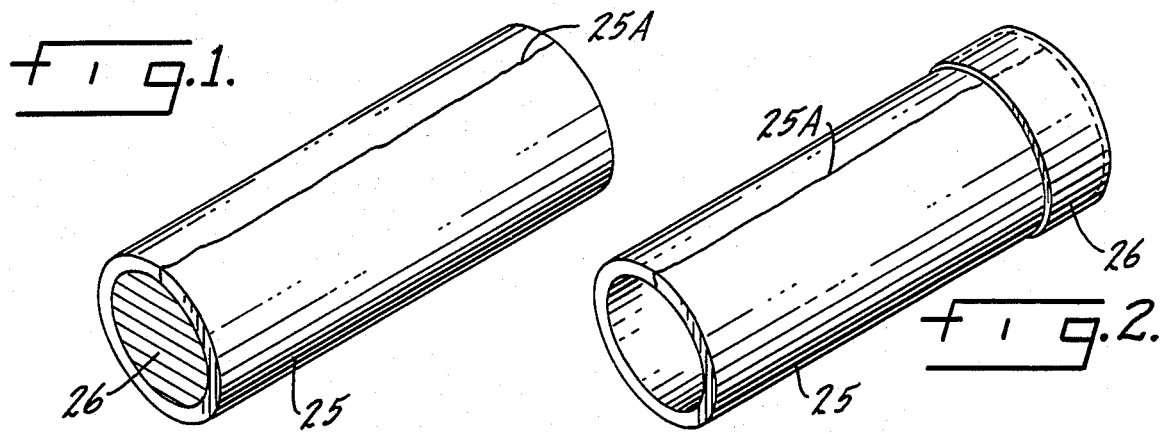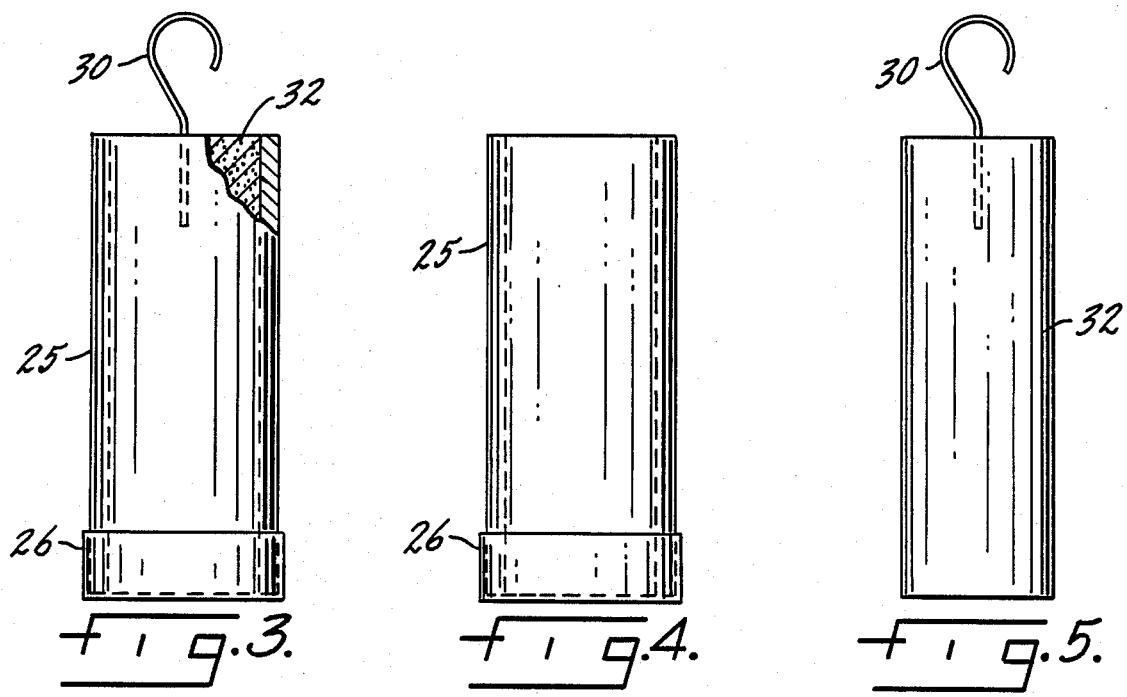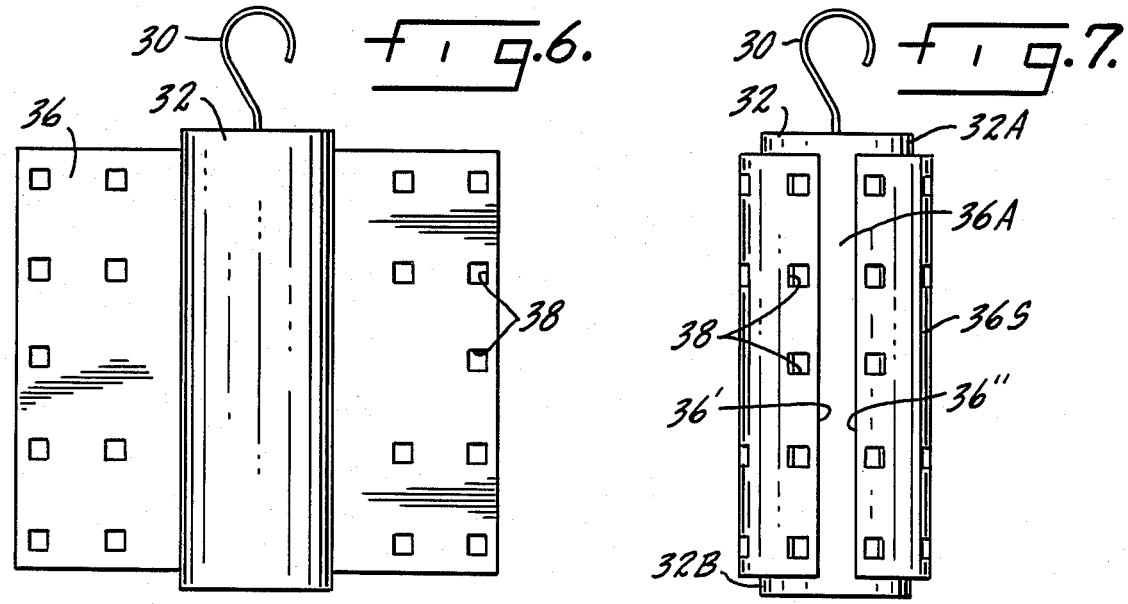

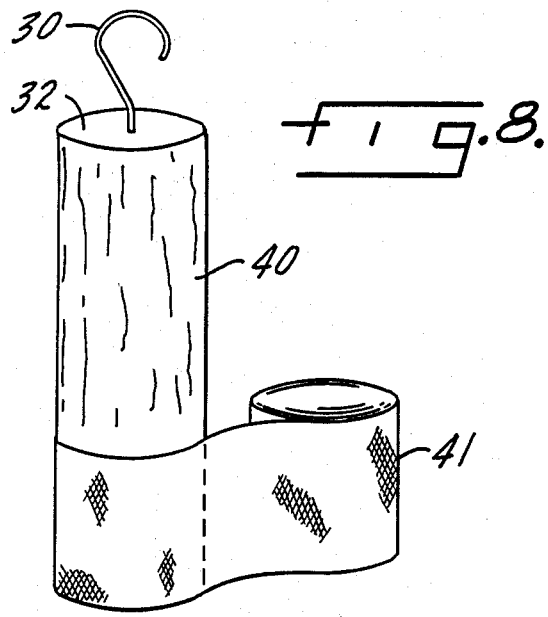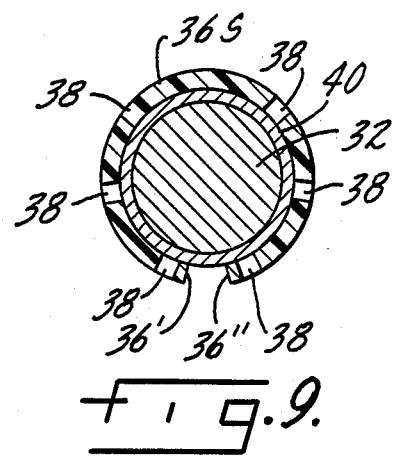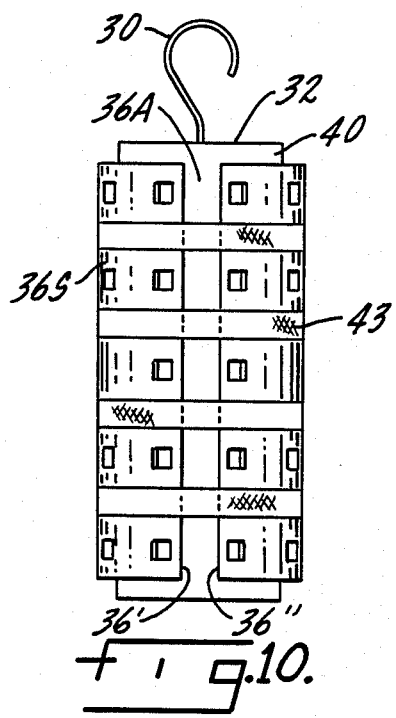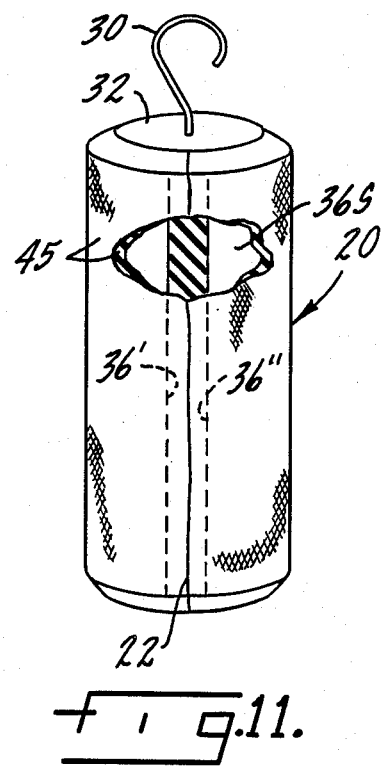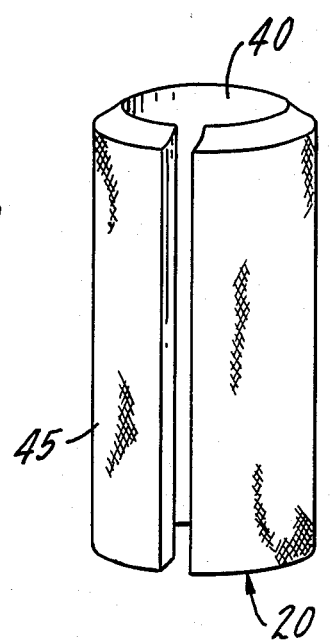

SOFT PLAYING ORTHOPEDIC SPLINT

This invention relates to an orthopedic soft playing splint, that is, a regulation-permitted, nonrigid splint for protecting an injury that is not disabling to the team player.

BACKGROUND OF THE INVENTION

Orthopedic playing splints (soft splints) are known, particularly for the hand, wrist or forearm. The injury is assumed to be one that is not truly disabling, that is, the player may be hurting plenty but he wants to play and can play with the aid of the soft splint. The splint must be soft since regulations prohibit hard splints.

Such splints have been made of silicone-impregnated gauze (of a width for the best anatomical conformation) allowing thick or thin splints to be made while wrapping and impregnating are alternated; protection against shock can be achieved by adding a urethane foam padding between layers of the splint as it is made, and after the cure of the silicone is complete the splint is split with surgical scissors, ready for use by refitting it with tape to the player at game time, or during practice; see The American Journal of Sports Medicine, Vol. 7, No. 6, page 358 et seq., 1979.

In another form, a plaster cast is made of the anatomy in the usual fashion. The cast is removed and is used as a hollow mold for a casting material; this material, after hardening, is removed from the plaster mold and the casting of course replicates the anatomy involved. The replicating casting is wrapped with gauze impregnated with room temperature vulcanizing rubber. When this sets, a concentric layer of foam is cemented to it and another layer of the rubber is employed as the outer surface. When the outer layer has cured, the structure is split, trimmed and fitted to the player as a soft splint; see The American Journal of Sports Medicine, Vol. 10, No. 5, page 293 et seq., 1982.

OBJECTS OF THE PRESENT INVENTION

The objects of the present invention are to assure that the soft splint will include a firmly anchored or locked foam pad positioned between layers of silicone rubber, to assure that the split edges are 100% silicone rubber so that none of the pad is exposed, and to assure that the ends of the pads are covered by silicone rubber, all of which contribute to a stable weatherproof splint which will withstand for a long time repeated use during the rigors of games and practice sessions, regardless of the weather. We ourselves attempted a similar soft splint but without these objectives being met, and the present splint is a considerable improvement compared to our earlier attempt.

DESCRIPTION OF THE DRAWING

FIG. 1 is a schematic perspective view of a plaster cast;

FIG. 2 is a view similar to FIG. 1 with the cast removed from the anatomical structure and capped at one end;

FIG. 3 is an elevation, partly sectioned, of the structure shown in FIG. 2 used as a mold and filled with a hardening castable material;

FIG. 4 is an elevation, similar to FIG. 3, with the mold removed from the casting;

FIG. 5 is an elevation of the casting separated from the mold shown in FIG. 4;

FIG. 6 is a view of the casting shown in FIG. 5, juxtaposed to a sheet of plastic;

FIG. 7 is a view showing the sheet of plastic wrapped as a sleeve about the casting shown in FIG. 6;

FIG. 8 is a perspective view showing the development of the inner silicone (rubber) sleeve;

FIG. 9 is a sectional view;

FIG. 10 is a view showing the intermediate sleeve secured to the inner silicone sleeve which itself surrounds the anatomical casting;

FIG. 11 is a a perspective view showing the completed splint, though it is one still surrounding the anatomical casting; and FIG. 12 is another view of the completed splint.

DETAILED DESCRIPTION

The completed soft splint is shown in FIG. 11, identified by reference character 20, ready to be removed from the internal core or casting. The preceding progression of steps for completing the splint will be described below but it may be mentioned in connection with FIG. 11 that the soft splint 20 has been cut along line 22 so that it may be spread and separated from the internal casting. After thus being removed, the soft splint may be further spread or opened, FIG. 12, so that it may be slipped over the anatomy to be protected. Application of this orthopedic device is completed by taping the slit and then wrapping the splint about the exterior with an ACE brand (expandable) bandage, taped in place.

It should be understood in connection with the description to follow that no particular form of anatomy is attempted to be depicted. In most instances, the device will be applied to the hand and wrist as a protective measure for injured joints. The anatomy of the hand and wrist is difficult to depict. However, it may be assumed in connection with the present drawing that the player has suffered an extreme trauma to one of the bones around the wrist area, painful in itself but not necessarily incapacitating the player. The soft splint, in such an instance, would be employed to reduce the risk of further injury.

Referring to FIG. 1, an ordinary plaster cast 25 is made preferably by employing a roll of three inch plaster impregnated gauze (e.g. Johnson & Johnson) which will harden in about ten minutes. The cast is then removed from the anatomy 26 in the usual fashion by slitting it along a line 25A opposite (lateral to) the injured area.

Before making the cast, the anatomy (e.g. the forearm) should be covered with a so-called stockinette and after removal of the cast 25 the clinging stockinette is removed from the inside, following which the inside of the plaster cast 25 is coated with petroleum jelly.

The next step is to use the cast 25 as a mold, to make a casting which of course replicates the anatomy, the forearm for example. In undertaking this step, the distal end of the initial cast 25, FIG. 2, is covered with a flexible cap 26 which may be nothing more than a surgical glove, secured by a strip of tape, not shown.

With the interior of the plaster mold lubricated and the distal end covered, plaster of Paris 32 may then be poured into the mold 25. A hook 30, FIG. 3, is quickly inserted into the hardening plaster of Paris at the proximal end, allowing the structure to be suspended when completing the steps hereinafter described.

The plaster of Paris will harden in two to three hours with the hook in place, whereupon the mold, FIG. 4, is removed from the resultant casting 32, FIG. 5; the casting 32 is cleaned.

The next step is to juxtapose a sheet of molding or moldable foam plastic 36 (one-half inch thick) to the anatomical replica 32. This sheet or padding is preferably a PLASTIZOTE brand moldable plastic which is simply a thermoplastic cross-linked polyethylene which is available from AliMed; it cures under mild heat to hold its shape. It may be flexed, after being molded to shape, but will return to shape.

In accordance with the present invention, it is important that the pad 36 be provided with perforations or openings 38 (one-half inch on a side and about two to three inches apart) serving the purposes hereinafter described. As shown in FIG. 7, the sheet 36 when fitting the casting 32 will have the edges 36' and 36" parallel to the axis of the anatomy spaced apart by about one inch and the resultant sleeve 36S shall be short at both ends by about one-half inch. The one inch spacing presents a longitudinal space or channel 36A. Thus when the sized sheet or pad 36 is folded or wrapped about the casting 32 to define the sleeve 36S, FIG. 7, and centered on the long axis, free end portions 32A and 32B of the anatomical replica 32 will project beyond the free ends of the sleeve 36S for a reason to be explained. The assembly of the casting and sleeve (FIG. 7) may then be oven-cured so that the sleeve 36S will hold its shape; it may then be separated from the casting so that the innermost rubbery layer of the soft splint may be formed as will now be described.

Referring to FIG. 8, the casting or core 32, while suspended by the hook, is covered from one end to the other by using a tongue depressor as a spatula to apply a layer of air-curing silicone rubber 40. There are several commercially available air curing (air vulcanizable) silicone compositions available on the market (along with the catalyst or accelerator to be mixed in) which may be used for this purpose. They are termed RTV silicones (room temperature vulcanizable) but we prefer to use the product of General Electric Company, identified as M.R.T.V. 7. The particular silicone rubber chemistry is not part of the present invention, nor the curing agent which will be used therewith at the time of mixing, immediately prior to applying the silicone layer. Thus, as already mentioned, silicone rubbers have heretofore been employed in making soft splints.

Before the innermost silicone coating has vulcanized, the sticky coating 40 is wrapped convolutely with a layer of gauze 41 (half width overlap) preferably a four inch Kling gauze. This is done under tension so that the gauze will become thoroughly saturated with and immersed in the silicone rubber as it vulcanizes. The cure or vulcanization is complete in about four to six hours, after which a second coating of RTV silicone rubber is applied. When the second coating is sticky, after about two hours, the previously prepared cylinder or sleeve 36S is then slipped over the the wet silicone sleeve (the silicone and gauze thickness, combined, become the inner layer 40) and the sleeve or pad 36S is centered, as above described, so that the silicone layer 40 is exposed for about one-half inch at each end. Also the intermediate sleeve or pad 36S will present the cavity or recess 36A, as above described, and as indicated in FIG. 10.

The intermediate sleeve 36S is then secured by tape strips as 43, and it should be mentioned that care is also taken to assure that the space or separation areas 36A will be opposite the injured area to be protected. A cross-section of the structure at this stage is shown in FIG. 9.

With the sleeve padding 36S in place, as shown in FIG. 10, a third layer 45 (external or outermost layer) of RTV silicone rubber is applied, taking care to fill the space or cavity area 36A thoroughly, the holes 38 in particular, and to fill in the pad deficit at each end so that the ends of the sleeve 36S are amply covered or sealed off by silicone. A single layer of four inch gauze is applied as in the previous step before the outer silicone layer 45 has hardened, that is, while it is sticky. Again, the gauze is impregnated with or immersed by the silicone before it sets.

At this stage a cross section would show a core 32 representing the anatomical replica, an inner layer of gauze-impregnated silicone 40, the intermediate sleeve of soft plastic 36S (see FIG. 9), an outer layer of gauze-impregnated silicone rubber 45 covering the sleeve 36S, and a seam entirely of silicone filling the channel or separation 36A, as may be gathered from FIGS. 11 and 12.

The structure is now nearly complete and the splint is allowed to cure overnight or for twelve hours, after which a fourth and final (cosmetic) coat of silicone rubber is applied, covering any exposed gauze threads to afford a smooth outer coat which, functionally, is not essential except that it does prevent fraying of the last gauze strip. The final coat is cured within a six to eight hour period.

The splint is then slit along the line 22, FIG. 11, which is to be medial of the silicone seam which fills the separation area 36'-36". Being thus split medially and fully cured, the splint may be spread apart to remove the internal core 32. The splint may now be spread and applied to the anatomy as above described.

The opening 38 and silicone seam are important. the openings allow the foam sleeve 36S to be locked or keyed to the inner silicone-gauze layer 40, because the foam sleeve is applied before this inner layer of silicone has set. Thus, small but important amounts of the inner silicone rubber exude and extend into the openings 38 of the pad.

The openings 38 also allow the sleeve 36S to be locked to the outer silicone-gauze wrapping 45 when it is applied.

When the final slit is made, medially down the silicone seam area, FIG. 11, the exposed edges are entirely silicone, so that the intermediate foam sleeve is protected against fraying or deterioration at the split. The keys or locks of silicone within the openings 38 also assure the sleeve 36S does not slip and this avoids any need of a separate step to apply a cement or caulking compound to assure the intermediate sleeve stays in place. Thus the sleeve is effectively immobilized without the need for any separate cementing step. By having the sleeve axially short, to expose about one-half inch of the casting 32 at each end, FIG. 7, this allows the circular ends of the sleeve 36S to be sealed and capped off by silicone. Finally, as to the foam sleeve itself, this affords additional soft padding to protect the injury and adds flexibility (softness) to comply with game regulations.

We claim:

1. In an orthopedic soft playing sleevelike, cylindrical splint to protect an injury, developed by first making a hollow cast of the anatomy to be protected and then using the cast as a mold for a castable material which hardens to replicate the anatomy, the improvement comprising an inner layer of gauze impregnated with an inner layer of a room temperature vulcanizable silicone rubber the inner surface of impregnated gauze replicating the outer surface of the anatomy, an intermediate sleeve of foam plastic applied concentrically to and partly immersed in the vulcanizable silicone rubber at the outer surface of said inner layer, said sleeve having spaced parallel edges defining a separation channel and also having large openings manually cut therein into which some of the silicone rubber of the inner layer is exuded to key the sleeve to the inner layer without the need for cement, and an outer layer of gauze wrapped about said sleeve and impregnated with an outer layer of room temperture vulcanizable silicone rubber with some of the silicone rubber of the outer layer exuded into said openings to key the sleeve to the outer layer without the need for cement, said separation channel being filled with silicone rubber, and the splint being slit along the length of the filled separation channel substantially medially thereof so the splint when spread and slipped over the anatomy to be protected exhibits separate channel edges of silicone rubber which protect the channel edges against gauze fraying and foam plastic deterioration.

2. The splint of claim 1 in which the outer layer of silicone is extended to cover longitudinal ends of the intermediate foam sleeve.

3. The splint of claim 1 in which the channel is lateral to the injury.

4. The splint of claim 2 in which the channel is lateral to the injury.

* * * * *